United States Patent [19]

Harden

[11] Patent Number: 4,675,018
[45] Date of Patent: Jun. 23, 1987

[54] SYRINGE MARKER

[76] Inventor: Dan J. Harden, P.O. Box 1345, Garden Grove, Calif. 92642

[21] Appl. No.: 853,733

[22] Filed: Apr. 18, 1986

Related U.S. Application Data

[63] Continuation-in-part of Ser. No. 712,686, Mar. 18, 1985, abandoned.

[51] Int. Cl.⁴ ............................................. A61B 19/00
[52] U.S. Cl. .................................... 604/407; 604/218; 141/27
[58] Field of Search ............... 604/187, 189, 207, 218, 604/211, 111, 407; 141/25, 26, 27; 128/765; 222/23

[56] References Cited

U.S. PATENT DOCUMENTS 2,224,018 12/1940 Holtman ............................... 604/218

Primary Examiner—John D. Yasko
Attorney, Agent, or Firm—Willie Krawitz

[57] ABSTRACT

A syringe marker is provided which comprises an internal plug that fits around the syringe plunger within the barrel. The marker is factory adjusted so that it is positioned adjacent the compression head of the plunger in the extended position. When the plunger is retracted to remove a pharmaceutical solution from a package or container, the marker will be moved back by the compression head to a point adjacent a scale marking on the barrel. This will indicate the volume of liquid contained in the syringe barrel.

1 Claim, 3 Drawing Figures

SYRINGE MARKER

This application is a continuation-in-part of U.S. Ser. No. 712,686, now abandoned filed Mar. 18, 1985, inventor: Dan J. Harden.

BACKGROUND OF THE INVENTION

This invention relates to a new and improved syringe, and more specifically to a marker for a syringe which is simple in construction and inexpensive to install. The syringe may be used by individuals who have a need to receive accurate doses of pharmaceuticals such as insulin, etc. Frequently, insulin users have difficulty reading fine scales, and this becomes even more of a problem when the solution to be measured is transparent when viewed against the scale. On a daily basis, it is obviously important that the user be accurately aware of how much dosage has been taken. Consequently, some measuring system is desirable which is effective, accurate, simple, and does not add appreciably to the cost of a hypodermic syringe.

In addition, patients frequently forget whether they have taken an insulin (or other) dosage, and it would be useful to have some type of highly accurate reminder of this fact.

THE INVENTION

According to the invention, there is provided a hypodermic syringe and marker, and method of use for indicating the surface location of liquid which has been drawn into the syringe. The marker is positioned around the stem of the plunger element, and when manufactured, is positioned in contact with the compression portion of the plunger. Consequently, when the plunger is drawn up into the syringe barrel during liquid uptake, the marker will be pulled along by the compression head and come to rest adjacent to a point of a measuring scale imprinted on the barrel, at the completion of the desired length of uptake stroke. Hence, the user will not have any difficulty reading the marker adjacent the measuring scale even though the liquid being measured is transparent and not readily discernible by some individuals who are diabetics. Obviously, the presence or absence of the marker within the upper portion of the barrel will indicate whether a dosage has been taken during a given period.

DESCRIPTION OF THE PREFERRED EMBODIMENTS

Figure 1:
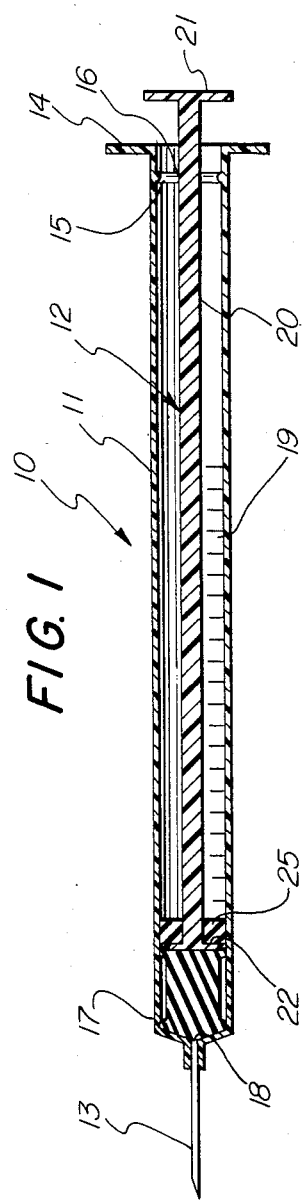
FIG. 1 is a cross sectional view in axial section of the syringe showing the plunger and marker prior to the uptake of liquid pharmaceutical.
Figure 2:
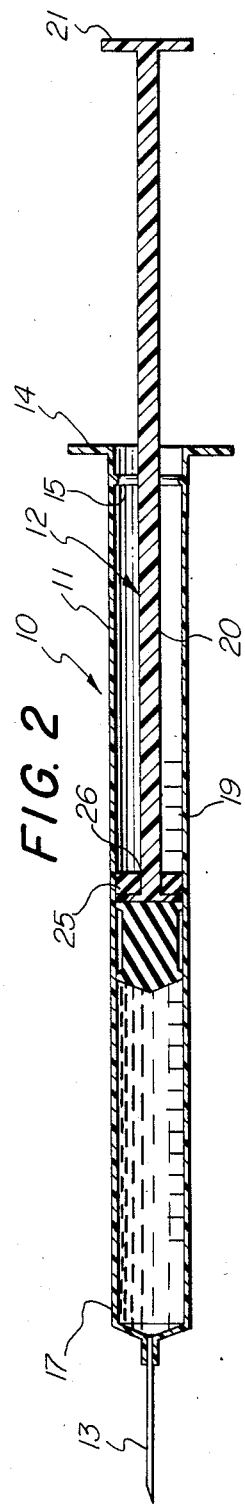
FIG. 2 is a view similar to FIG. 1 showing the plunger and marker following the uptake of liquid pharmaceutical; and, FIG. 3 is a view similar to FIGS. 1 and 2, showing the device following depression of the syringe plunger leaving the marker in place in the barrel, and functioning as a volumetric reading.
Figure 3:
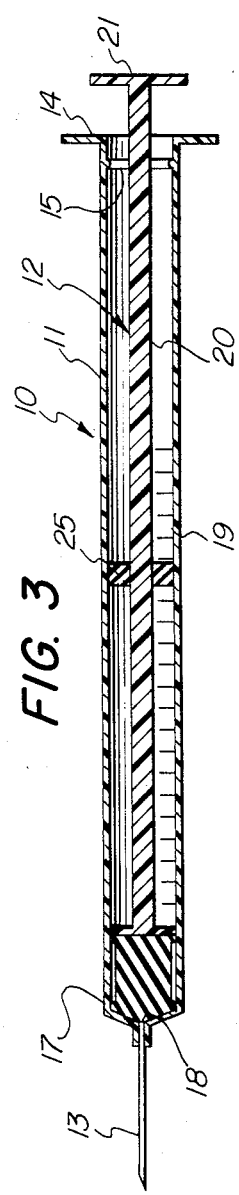

The hypodermic syringe and marker assembly 10 of this invention is shown in FIGS. 1-3, and comprises a barrel portion 11, plunger element 12 and needle 13. The barrel 11 may be constructed of a suitable sterilizable clear plastic such as polypropylene, polystyrene, polyester, etc. The barrel includes an upper flange member 14, an internal gasket 15 having a guide bore 16, and a hub portion 17 for securing the needle 13 therein.

A central bore 18 in the hub connects the hollow portion of the needle with the interior of the barrel. A scale 19 is inscribed on the outside of the barrel to measure liquids therein. For barrel capacities of 1-12 cc., typical internal diameters will vary from about 180-625 mils. The plunger element 12 comprises an elongate stem portion 20, flange 21, and compression head 22; the stem 20 passes through and is guided by the guide bore 16 of the gasket 15. A marker 25 having a bore 26 is slidingly mounted on the stem portion 20 of the plunger element 12, and is constructed of a suitable material.

When the syringe is manufactured, the plunger is in the fully extended position, and the marker is positioned adjacent to, and in contact with the compression head 22. Therefore, when the plunger is retracted by the user to intake liquid pharmaceutical from a container or package, the compression element 22 will move the marker upwardly. At the end of the desired length of uptake stroke, the marker will come to rest at a given location adjacent the scale 19. The volume occupied by the compression head and marker within the barrel will of course be compensated by adjustment of the scale position. When the user then depresses the plunger element 12, to inject pharmaceutical, the marker will remain in place. Although the syringe is not intended for reuse, the location of the marker within the barrel enables the liquid volume to be easily read, and it serves as a reminder that a dose has been taken. The marker also may be used for multiple dose syringes.

At the end of a dosage period, all used syringes are discarded. This prevents confusion when determining if a dose has been taken during a subsequent dosage period, usually the following day.

I claim:

1. A method of reading the scale of a hypodermic syringe, comprising:
  A. intaking a pharmaceutical fluid into a hypodermic syringe, the syringe comprising:
    (a) a barrel portion for retention of a pharmaceutical liquid, the barrel providing a scale inscription;
    (b) a hub portion mounted at one end of the barrel and providing a bore therethrough;
    (c) a hollow hypodermic needle mounted in the hub, the bore of the hub connecting the barrel and needle;
    (d) a plunger mounted within the barrel for intaking and ejecting pharmaceutical liquid, the plunger including a stem portion and a compression head; and,
    (e) a marker inside the barrel to determine the maximum level of liquid drawn into the barrel by the plunger, the marker being disposed aorund the plunger stem and slidably moveable therealong, and being positioned adjacent to, and in contact with the compression head of the plunger when the plunger is in a depressed or intake position;
  B. raising the plunger and compression head to intake pharmaceutical liquid, thereby moving the marker along the barrel and adjacent the scale, to indicate the amount of liquid intake; and,
  C. reading the location of the marker against the scale when the marker remains in place following depression of the plunger and compression head to eject the pharmaceutical liquid from the barrel and out through the needle.

* * * * *